United States Patent [19]

Hepp et al.

[11] Patent Number: 4,669,483

[45] Date of Patent: Jun. 2, 1987

[54] LITHOTRIPSY SYSTEM HAVING LOCATING AND ORIENTING APPARATUS

[75] Inventors: Wolfgang Hepp, Immenstaad; Karl-Heinz Restle, Tettnang; Dick van Rijn, Eriskirch; Othmar Wess, Immenstaad, all of Fed. Rep. of Germany

[73] Assignee: Dornier System GmbH, Fed. Rep. of Germany

[21] Appl. No.: 757,068

[22] Filed: Jul. 19, 1985

[30] Foreign Application Priority Data

Jul. 21, 1984 [DE] Fed. Rep. of Germany ....... 3427001

[51] Int. Cl.[4] .................. A61B 10/00; A61B 17/22
[52] U.S. Cl. .................................. 128/660; 128/328
[58] Field of Search ................ 128/24 A, 328, 600, 128/804, 303 R

[56] References Cited

U.S. PATENT DOCUMENTS

| | | | |
|---|---|---|---|
| 4,341,222 | 7/1982 | Gardineer et al. | 128/660 |
| 4,485,819 | 12/1984 | Igl | 128/660 |
| 4,610,249 | 9/1986 | Makofski et al. | 128/328 |

*Primary Examiner*—Kyle L. Howell
*Assistant Examiner*—Francis J. Jaworski
*Attorney, Agent, or Firm*—Ralf H. Siegemund

[57] ABSTRACT

An improved shockwave lithotripsy system includes a movable patient support carriage having a shock wave generator and focussing device mounted thereto, along with an indexing reference. An ultrasonic oscillator is also attached to a mounting arm arrangement mounted in turn to the support carriage and allowing for three dimensional adjustment of the oscillator relative to a patient on the carriage, the mounting arrangement having an additional indexing reference such that after a concrement internal to the patient is located using the ultrasonic oscillator, the shock wave generator may be brought into focus on the concrement by bringing the indexing references into registry.

8 Claims, 2 Drawing Figures

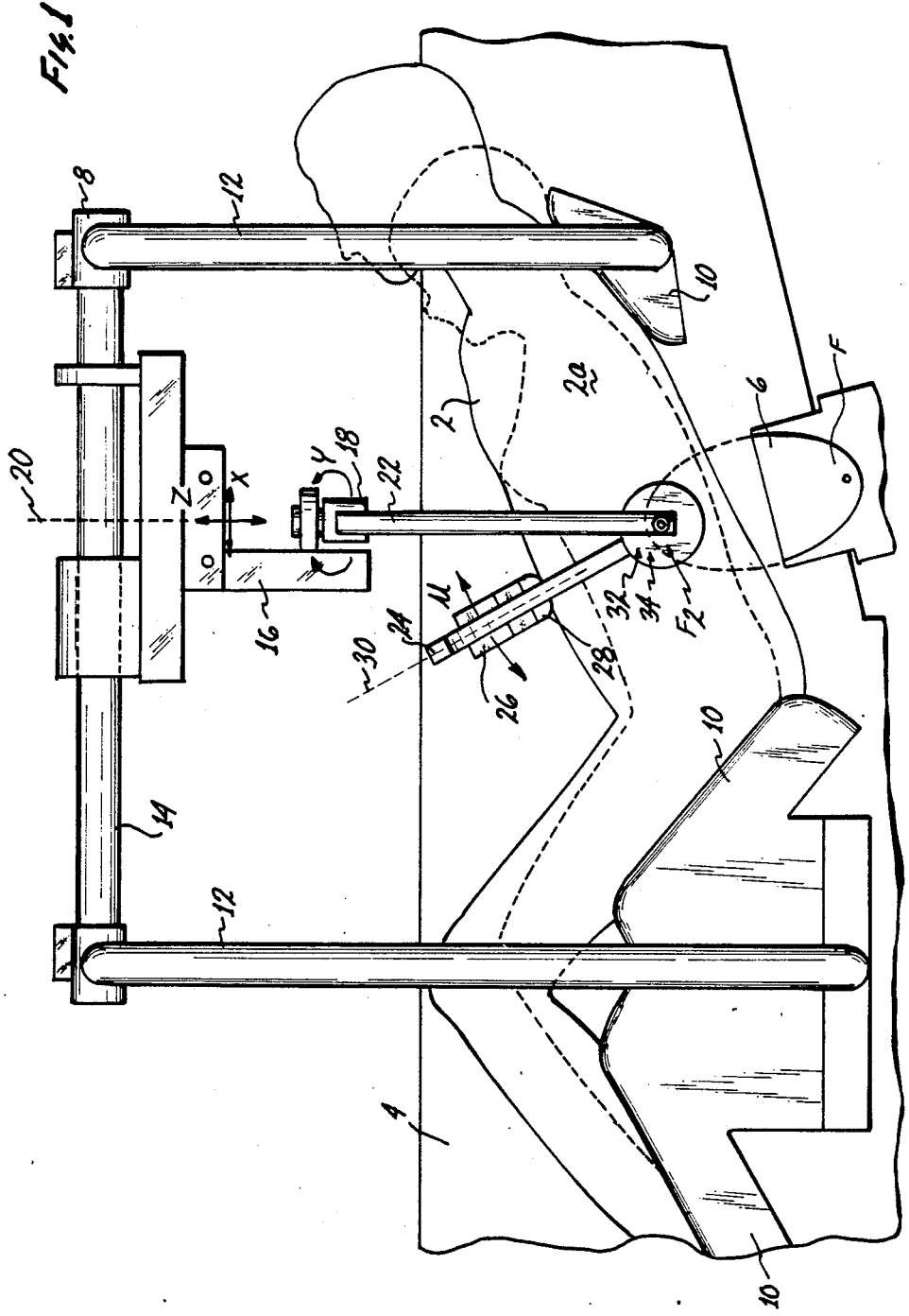

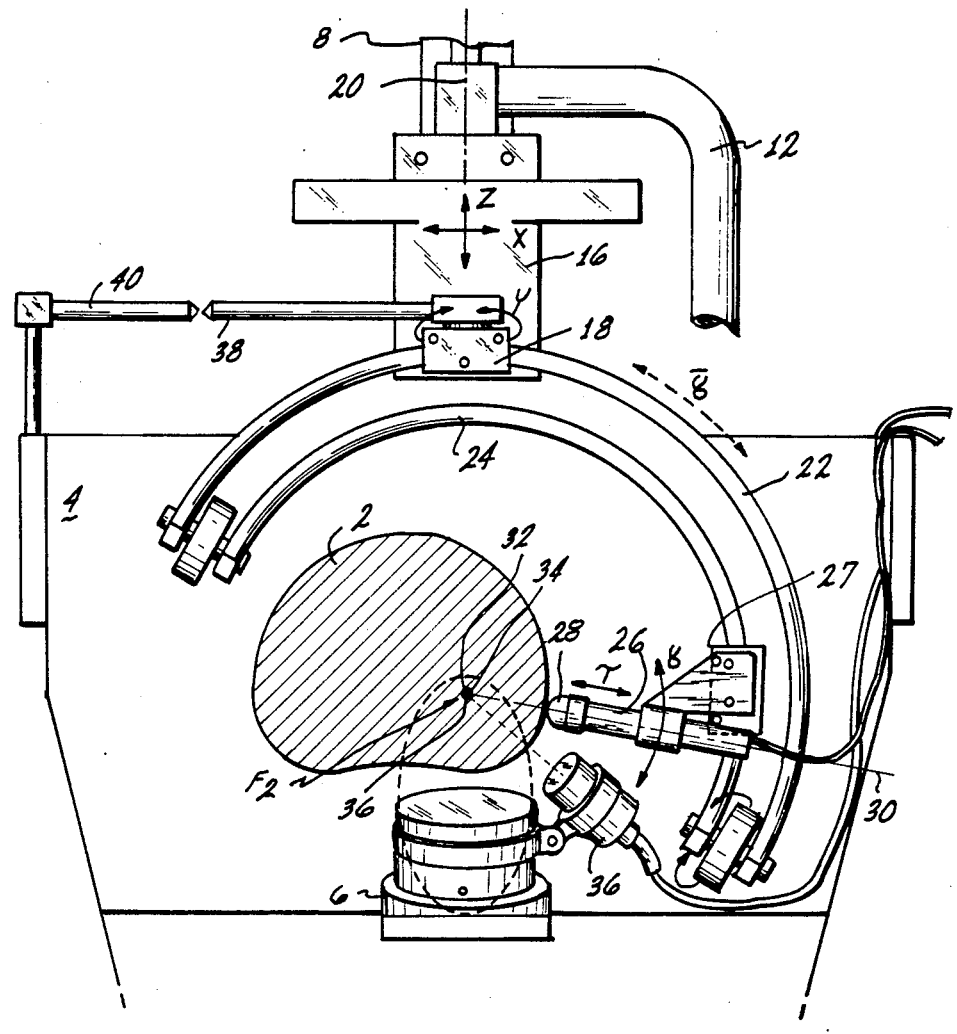

LITHOTRIPSY SYSTEM HAVING LOCATING AND ORIENTING APPARATUS

BACKGROUND OF THE INVENTION

The present invention relates to a preparatory locating procedure and positioning of a device to be used in conjunction with a non-invasive comminution of concrements in the body of a living being, under utilization of shock waves for purposes of the comminution proper (extra corpo real shock wave lithotripsy), while ultrasonics are to be used for the locating purposes.

German Pat. No. 23 512 47 (see also U.S. Pat. No. 3,942,531) discloses a device for the comminution of concrements in the body of a living being under utilization of a shock wave source. This source is placed in a first focal point of a focusing chamber being constructed as part of a rotationally symmetrical ellipsoid and being positioned so that the second focal points coincides with a concrement. The shock wave is usually produced by way of spark discharge. The practicing of comminution of kidney stones, without operative (invasive) procedure, and without the introduction of probes has been successfully practiced. An extensive description of equipment and therapeutic procedure is for example found in "Extracorporal shock wave lithotripsy", Ch. Chaussy ed., Munich 1982.

This kidney lithotripter was delivered in the beginning of 1984, by applicant's assignee and uses as a locating device two X-ray systems, in order to determine the exact position of the kidney stone, and in order to determine also its size. This locating procedure is also for example described in "The Dornier Kidney lithotripter" ZMV2 07-8403500. Once having located at least approximately the particular concrement such as a kidney stone the patient is shifted vis-a-vis the shock wave generating and focusing system for purposes of positioning, so that indeed the stone will coincide with the second focal point of the focusing chamber. Having located the particular stone and having placed the patient in the particular position necessary for a successful comminution process, the shock waves are triggered and the stone is in fact comminuted into a fine grit. Natural process of the body flushes the particles out of the system. The device for producing the shock wave field as well as the locating equipment are arranged so that they will not mutually interfere with each other as far as their individual function and purpose is concerned.

Typically, the two X-ray devices for locating the kidney stone are disposed next to the shock wave generator and reflector and on, so to speak, opposite sides or an axis of the generator. The two central beams of the two X-ray equipments intersect the axis of the reflector running through the two focal points, and under an angle of about 40 degrees each; the intersection of course should be situated near or right in the location of the kidney stone. Essential is a kind of orientation fixing which establishes a spatially fixed and thus structural unity between X-ray locating and patient/shockwave generating equipments; everything has to be moved vis-a-vis the patient. It is apparent that from an equipment point of view, the utilization of two full X-ray equipment and devices is relatively expensive. Moreover this utilization entails cutting into the reflector or portions thereof the windows which permit the passage of X-rays. And last but not least the patient receives, so to speak, a double dosage of X-rays.

Between the body and the reflectors along the shortest path into the body from the reflector, one usually provides a certain water coupling path in order to make sure that the shock wave propagating medium, namely water, does not substantially change in between the two focal points. On the other hand placing water in between the body and X-ray equipment deteriorates the performance of this locating equipment, so that care has to be taken that the X-rays will not pass through water. Alternatively certain steps have been taken in the past towards restricting the water path between the shock wave equipment and the body so as to avoid passage of X-rays through water.

As an alternative the locating and positioning, procedure as defined, ultrasonic is suitable and practical for a variety of reasons. As far as positioning the concrement is concerned, i.e. shifting either the body or the concrement itself in one form or another, ultrasonics is comparatively slow and, therefore, not as desirable or reliable as X-rays are, because the search process is difficult under utilization of a mechanical oscillator being fixed in relation to the shock wave lithotripter. It has to be considered that, so to speak, the human body has also ultrasonic entrance windows, which poses limitations in the application of ultrasonics for purposes of generating images representative of the interior or interior portions of the human body. The various organs and their movement are aspects which limit so to speak this window. Also, it is not only necessary to find the right spot on the surface of the human body through which ultrasonics and shock waves may enter but one needs the proper direction so as to bypass impediments of that window (keyhole effect).

DESCRIPTION OF THE INVENTION

It is an object of the present invention to provide a new and improved locating and positioning device and equipment to be used in conjunction with noninvasive comminution of concrements in the body of a human being and which permits real time observation of any concrement, is economical and provides for a rapid and reliable locating procedure which even is capable of finding concrements that seem to be covered in one form or another or hidden and which moreover provides a rapid and reliable positioning of the body in relation to the shock wave system or vice-versa on the basis of the detected position and location of a concrement.

It is a feature of the present invention to develop structurally locating and positioning procedures so that concrement locating can independently proceed first, followed by a positioning procedure for the shock wave generator.

In accordance with the preferred embodiment of the present invention it is suggested to provide a guide in which an ultrasonic source and receiver is slideable and pivotable to cover a relatively large area of the body of the human being, and structure is provided to mark or index and register the position, possibly also the direction of operation of the ultrasonic source vis-a-vis the concrement, so as to permit subsequent indexing by mechanical or electronic correlation of the position of the concrement with the focal point of the shock wave system.

In accordance with the invention, then, a commercially available or a specially made ultrasonic scanner or ultrasonic imaging system with mechanical oscillator can be used. This device is to be placed on any spot of a particular area of the body, for example the upper abdomen, remaining variable as to orientation and without losing its relative orientation in relation to the shock wave generator and the focal point system thereof in particular. The oscillator, i.e. the ultrasonic imaging device is freely moveable just as if it were held by hand.

Searching for and imaging in some form concrements is analogously possible as compared with daily medical practice of ultrasonic diagnostics. The information about the exact spatial position of the concrement vis-a-vis a fixed point in space, such as the focal point of the shock wave system can be extracted from the ultrasonic image provided that simultaneously three coordinate values for the actual position of the oscillator as well as the direction of these coordinates is registered or marked in some fashion and/or calculated for purposes of generating position control signals. So called compound scan arms for purposes of generating ultrasonic images are capable of ascertaining the aforementioned coordinates. If for example a sector transducer is fixed to such a scan arm a continuous ultrasonic image can be made available even without movement of the scan arm, which is different from the usual compound practice.

The coordinates for determining the particular position are acquired through suitable angle and position measuring transducers. These values must be correlated in a computing fashion with target information on the ultrasonic imaging device. The result is a distance value between target (concrement) and shockwave generator (focus), the result further includes representations of a direction along which the shock wave focus must be moved so as to obtain coincidence between concrement location and shock wave focus for, permitting controlled application of shock waves right in the concrement.

The inventive principle can be briefly summarized as follows: a locating center in relation to which the ultrasonic imaging system is adjusted is brought into coninicidence with a concrement; the shock wave generator is then positioned so that its focal point of concentrated shock wave action will coincide with that locating center.

In an advantageous embodiment the inventive correlation does not necessarily require electronic acquisition and processing of data to arrive at control signals, by means of which the positioning can thereafter be obtained mechanically. Broadly speaking the following concept is used. For purposes of positioning it is necessary and sufficient to know the three spatial coordinates of the concrement at any given point in time. These spatial coordinates can be designated by X, Y and Z. The concrement is to be imaged by ultrasonic process. In order to obtain the best possible and practical imaging, the oscillator, i.e. the ultrasonic wave source and receiver has to be placed in relation to various, basically unforeseeable parts of the human body with as free as possible an orientation that can be obtained. This aspect involves particularly the orientation of the oscillator vis-a-vis an appropriate "entrance window" in the body and the direction of the ultrasonic beam must be directed towards, into and through that window. In accordance with a preferred form of practicing the invention the moveability of the oscillator and here particularly the angular adjustment thereof is obtained by causing the oscillator through an appropriate guide structure to move on and along the surface of a sphere, while the oscillator remains oriented towards the fixed center of that sphere.

A possible form of practicing the invention is a cardanic suspension, whereby the oscillator is moved along an arc and this arc itself can be pivoted. This way it is possible to orient the axis of the oscillator from any given direction in relation to the concrement which is supposed to be located, to appear in the center of that sphere. Through this procedure one can search for and adjust towards the most advantageous entrance window of the body, whereby "advantageous" is to be understood vis-a-vis the anatomy of the human body.

The arrangement which moves the ultrasonic oscillator vis-a-vis a centr must by and in itself be freely adjustable along the three spacial coordinates, so as to situate the center of that sphere at or even in the concrement. Matching of the entrance window and the direction of observation for the concrement of interest involves a three dimensional angular adjustment of the oscillator about that center. As soon as the concrement appears in the ultrasonic image and at a particular well defined location therein, particularly as far as the image screen and the imaging process generally is concerned the spatial coordinates X, Y and Z as such fix the position of the concrement in space.

An X, Y, Z positioning system can now be operated independently from the direction of observation, simply for example through a fixedly connected marking arm that causes the spatial position of the concrement relative to the patient to be marked in some visible fashion. This marking now must be followed up by another step, namely by establishing a specific relation to a second marking which signifies the operative center of the lithotriptor, i.e. the focal point in which the focusing device centers and concentrates the shock waves.

Once the center of shock wave application is made to coincide with (a) the center of adjustment of the ultrasonic imaging equipment and (b) the concrement, having been previously positioned in that center, it is now possible to trigger the shock wave process to be effective with certainty at the desired and adjusted location. All these steps as delineated can be carried out by hand, simply through observation of the imaging screen and by observing suitable representations of the various markings outlined above. On the other hand since the markings and the concrement are made visible, signal representation can be acquired from the ultrasonic imaging equipment and from the markings, so that the positioning control as such can be carried out automatically through suitable follow-up control.

It follows therefore, that without limiting the range of moveability as to pivot angles and spatial coordinates X, Y and Z these adjustments are coupled to each other such that each motion of the ultra sonic imaging oscillator is subdivided into a translatory movement in and along the three coordinates X, Y and Z and into turning and pivoting motions necessary for obtaining the requisite positioning and orientation. One has to be mindful that the center proper of turning the various parts is in fact located inside the patient and therefore not accessible directly. This virtual point being the inherent equipment center is made to locate in the body of the patient.

The inventive equipment is particularly suitable when used in conjunction with a water tub into which the patient is partially submerged and includes a rest on which he or she has been placed, because under such circumstance, no immediate and direct contact between the ultrasonic oscillator and the human body is necessary. The water in the tub serves adequately as a coupler path for the ultrasonic energy as it is coupled into and out of the human body for the imaging process.

If however a tub is not used the invention can still be practiced for example in conjunction with a coupling cushion, making it necessary to bring the ultrasonic equipment more or less directly in contact with the body. This is obtained in that the oscillator is moveable axially in an appropriate holding device so that the oscillator can be moved in relation to the common center as defined above, until there is contact with the surface of the body. For this, in turn the ultrasonic image will synchronously travel with the axial displacement of the oscillator vis-a-vis the center of the pivoting device, but remains always in the center of the image field (screen). Thus the center cannot be marked fixedly in the ultrasonic image as such rather it has to move synchronously with a marking in that axial direction. The actual axial position of the ultrasonic transducer can then be ascertained through a suitable tracking device that tracks the displacement motion of the ultrasonic head, and that in turn is used for positioning and marking.

The locating process in accordance with the invention is therefore to be seen in that the particular concrement is searched for and located by a kind of trial and error procedure until the concrement is caused to coincide with the center of the pivoting and positioning equipment for the ultrasonic transducer and variations in the direction of that transducer constitutes a search for the most suitable entrance window and for the orientation of the axis of the oscillator vis-a-vis the body. Once this coincidence between the center of the adjusting equipment for the ultrasonic imaging device and the concrement had been obtained, a second step causes that center to coincide with the center of shock wave action, that is the focus of the shock wave generator.

A particular advantage of the inventive equipment can be seen in that another degree of freedom remains selectible. Namely the ultrasonic section plane can be changed without any change in the adjustment obtained or obtainable as per the above delineated procedure; one simply rotates physically the ultrasonic transducer; since its axis runs through the center of the system, coincidingly adjusted vis-a-vis the central nut that rotation does not change the adjustment. The selection of the ultrasonic section plane can be made in accordance with different aspects. For example, the motion of organs and of the concrement in particular within the body and resulting for instance from breathing by the patient, is usually a motion that occurs in a particular plane and, therefore, the ultrasonic section plane can be adjusted to coincide with that plane. Once that adjustment is obtained one can continuously observe the motion of the concrement within that plane and in accordance with the oscillatory movement timing and phasing of shock wave triggering can be appropriately selected.

Another aspect for realizing the invention is to be seen in the utilization of a robot like arm with a sufficient number of hinges and pivot points so that three degrees of freedom for translation is provided for and the ultrasonic oscillator can in addition be made pivotable in all spatial directions. The arm with the ultrasonic oscillator at its end can be adjusted automatically or by hand, under observation of the ultrasonic image. As soon as the target concrement appears in the ultrasonic image its exact position can be ascertained, visually or automatically. Through evaluation of the then existing hinge adjustment in terms of angle, and/or through ascertained displacement by means of transducers, the exact position can indeed be attained automatically, or semi-automatically if the adjustment as such is carried out by hand under visual observation. In addition to the respective adjustment of the robot arm, the position of the target object in the ultrasonic image itself is to be considered. This is carried out as is customary already, through shifting of a visible marking on the monitor or image screen, to the location of the target image, which is an interactive mode of operating the imaging system as such.

DESCRIPTION OF THE DRAWINGS

While the specification concludes with claims, particularly pointing out and distinctly claiming the subject matter which is regarded as the invention, it is believed that the invention, the objects and features of the invention, and further objects, features and advantages thereof, will be better understood from the following description taken in connection with the accompanying drawings, in which:

FIG. 1 illustrates a device and arrangement constructed in accordance with the preferred embodiment of the present invention for practicing the best mode thereof, and wherein a patient is shown in side elevation; and FIG. 2 illustrates the same device but in section view as far as the patient is concerned, and in a direction of view as indicated by arrow II in FIG. 1.

Proceeding now to the detailed description of the drawings, the figures illustrate a body 2 of a patient, illustrating the patient in side view, particularly in FIG. 1 and in a section in FIG. 2. The patient is placed into a water filled tub 4. Simply in order to demonstrate versatility of the system, a smaller body is shown in dashed lines, identified by reference numeral 2a and superimposed upon the body 2. The smaller body may be represented e.g. by a child. The bottom of the tub 4 receives a partial ellipsoidal focusing device 6 for shock waves having an axis of symmetry which is slightly slanted in up direction. The focusing and shock wave generating device 6 is basically fixed to the tub 4, but may be adjustable thereto. However, for purposes of this invention, an invariant position relative to the tub 4 can be assumed.

The focal point F1 for this ellipsoid is assumed to be the point of origin of shock waves. Usually one uses spark discharges for that purpose. The chamber 6 focuses these shock waves into a second focal point F2, external to the focusing chamber. Please note, that F2 is shown to coincide with several other identified points. This represents, so to speak, the end phase of the operation to be explained. Initially, these various points do not coincide! Conveniently F2 is deemed an invariant reference towards which the other points can be adjusted. This is, however, just a convenient point of view. The coincidence is the main aspect, which points are adjusted in relation to each other as a matter of practicality.

The body 2 of the patient rests on a rest support with cushions 10 being held by carrier arms 12, which are suspended from a transverse carrier 14. The mounting structure is basically conventional (see lithotripter publications). The transverse carrier 14 serves also as the mounting facility for the invention locating and positioning device. The locating and positioning device is directly mounted on a carrier 16, which can be moved in three coordinate directions, X, Y and Z, relative to carrier 14, and wherein the Y direction stands transversely to the plane of the drawing of FIG. 1, while the X direction runs transversely to the plane of FIG. 2. As stated the carrier 16 is moveable in these three coordinate directions, and a guide 18 is fastened to the carrier and permits rotation about a vertical axis 20 through an angle denoted generally as phi. This constitutes a first angular direction of adjustment.

An outer, semi-circular rail 22 is mounted in and supported by the guide 18. An inner, likewise semi-circular rail 24 is mounted by its ends to the respective ends of the rail 22 so that the rail 24 is pivotable by an angle delta; the pivot axis extends in radial direction as far as this particular circular arrangement is concerned. The outer rail 22 is guided by (and driven by) guide 18 such that it can undergo colinear movement along its extension, thereby causing the rail 22 to rotate along angular displacement gamma-bar.

The inner rail 24 carries a slide or carriage 27 which in turn supports an ultrasonic oscillator image producing device and transducer 26 for a pivot motion thereof about an angle gamma. Strictly speaking, the adjustment by angles gamma and gamma-bar is redundant, but adds to the versatility of the system. The ultrasonic transmitter/receiver device 26 is urged by means of a spring against the body 2, there being a (water filled) coupler cushion 28 interposed. The ultrasonic oscillator 26 is additionally rotatable about its own main axis 30 which is of course the axis of emission of a central beam of ultrasonic waves. Moreover ultrasonic oscillator 26 is longitudinally moveable on and along this axis 30.

The entire device is constructed so that the angular displacements orient the ultrasonic oscillator 26 to always face towards a particular point which in this case is the geometric center 32 of the two semi-circular rails 24 and 22. Pivoting of the oscillator about axis 30 does not change the orientation vis-a-vis center 32; movement on axis 30 changes the distance from that center. The center 32 is thus inherent in the adjusting system: translatory adjustment adjusts it location; angular adjustment remains centered on that point.

The various parts may be provided with position sensing transducers such that the X, Y, Z adjustment, as well as any of the angular adjustments are represented by electrical signals to permit automation.

After having described the equipment, the locating procedure is carried out as follows. The attending and supervising physician turns on the ultrasonic oscillator 26 and looks at an ultrasonic imaging screen and monitor, which is not shown, but which shows a section through the patient at that point, which of course, is basically an arbitrary section, but is located in a plane that includes the axis 30. The attendant can now shift the ultrasonic oscillator 26 to various parts of the body and in various ways, there is a great degree of versatility in the adjustment. This means specifically that as the center 32 is moved by device 16 the ultrasonic oscillator 26 is thereby moved in the three coordinate directions X, Y, and Z, until the concrement 34 is visible on the monitoring screen. When the concrement 34 appears in the center of the monitor screen, the geometric equipment cente 32 coincides with the concrement. A hairline cross on the ultrasonic imaging screen may be positioned so that its center always corresponds to the center 32 and is oriented accordingly.

In addition, the device as suspended by mount 16 can be pivoted about a vertical axis 20 (angle phi); about an axis through arc displacement of the rail 22 along the direction gamma-bar; thirdly, the rail 24 can be tilted out of the plane defined by the rail 22, amounting to pivoting about an angle delta. Finally device 27 carrying the ultrasonic camera 16 can be shifted on rail 24 over angle gamma. This way the supervising physician can search for a suitable entrance window into the body of the patient, in terms of ulrasonic waves and he can also look for the most advantagous direction for ultrasonic direction for ultrasonic radiation. In all these cases the equipment remains centered as far as the ultrasonic oscillator 26 is concerned towards the point 32 which is the above defined center. It is emphasized however that at that point the center 32 and the concrement 34 coincide with each other but does not coincide with the focal point F2 of the shock wave generator. In addition the physcian can vary the distance r between the center 32 and the ultrasonic oscillator while he can rotate the ultrasonic section plane by rotating the oscillator about the axis 30.

In summary then, the physician of course will use the equipment primarily towards finding a concrement 34 and the will move the equipment and provide for the necessary tilting until the point and center 32 coincides with a concrement 34. It should be noted specifically that locating the concrement 34 as such involves primarily adjustment in the X. Y and Z directions. Once the center 32 has been adjusted it remains coincident with the concrement 34. The pivoting adjustments about angles phi, gamma-bar, gamma, and delta will not cause a change in that position, but merely change the orientation of the ultrasonic waves in relation to the concrement, which amounts to a search for the best direction from which to apply later on the comminuting shock waves. Having found such a concrement he may in addition rotate the imaging and section plane by rotating the oscillator 26 about axis 30 to cause that section plane to coincide with a plane in which the stone may move naturally for example on account of breathing by the patient. If in fact the section plane is adjusted in that manner, the concrement will remain visible in the ultrasonic imaging plane during the entire application of shock waves. Details of this particular aspect are disclosed and described for example in co-pending application U.S. Ser. No. 753,658 filed July 10, 1985 and having overlapping inventive entity.

Next the patient must be positioned properly in relation to the shock wave generator. For this the rest 8 is adjusted inside tub 4. Since the adjustment center previously described, reference numeral 32, now remains invariant with regard to that rest, while on the other hand the patient is more or less immobilized on the rest, the coincident relationship of center 32 and concrement 34 will follow that movement. Of course, some fine adjustment and tracking may be necessary if the patient on account of the movement of the rest, happens to move, or be moved for some reason or another in relation to the rest.

The adjustment of the rest with the patient, now provides that the focal point F2 of the shock wave generator and focusing chamber 6 is made to coincide with the coincident points 32 and 34. This is carried out by placing two particular markings or marking pins in a directly confronting and juxtaposing relationship. There is a first indexing pin 38 which is invariant with the X, Y, and Z adjusted structure 16, 18. The pin 38 does not change orientation upon any tilting by angles gamma, gamma-bar; phi and delta, there is a second indexing pin 40, whose tip is invariant with the focusing chamber 6 and the focal point F2 thereof. One can also say that each of the tips of the pins 38 and 40 bear a particular geometric relationship to other equipment, the tip of pin 38 has a specific geometric relationship to the center 32, and the tip of pin 40 has exactly the same relationship in terms of geometry vis-a-vis the focal point F2. Therefore once the two tips of the pins 38 and 40 face each other, not necessarily coaxially but are more or less juxtaposed or in engagement, one has thereby adjusted the focal point F2 to coincide with the geometric center of the adjusting device 32, which in turn was previously adjusted to coincide with the concrement 34. Locating and positioning are now completed.

Finally it should be mentioned that FIG. 2 illustrates a secondary ultrasonic oscillator and test head 36, which is arranged to have a fixed orientation vis-a-vis the focal point F2. However, it may be pivoted about the axis of focusing chamber 6, such axis being defined by the line between the two focal points F1 and F2. This second ultrasonic imaging equipment is provided with a higher resolution than the search oscillator and image generator 26. This device 36 permits supplemental, more, accurate, final adjustment and monitoring of the actual comminution process of the concrement 34, i.e. it serves as observation unit to observe what happens once the shock wave generator has been triggered. The higher resolution may be obtained through a larger aperture or through loss in depth of field.

The invention is not limited to the embodiments described above, but all changes and modifications thereof, not constituting departures from the spirit and scope of the invention are intended to be included.

We claim:

1. Locating and positioning apparatus for preparing a focusing shock wave system for the noninvasive comminution of concrements in bodies of living beings, comprising:

a patient support means for establishing a particular position of a body of a living being;

multi dimensional and pivotable mounting means for an ultrasonic oscillator connected to the support means;

an ultrasonic oscillator mounted to said mounting means; the mounting means permitting the oscillator to assume a variety of different positions vis-a-vis said support means for the body of the living being and the body on the support means;

first indexing means connected to the mounting mans for providing a reference representation of the position of the ultrasonic oscillator vis-a-vis a particular geometric point inherent in and established by said mounting means but outside of the mounting means, permitting through ultrasonic imaging, coincidence of said point with said concrement;

a shock wave system including a shock wave generator and focusing device mounted to the support means;

means including second indexing means, and connected to said support means and movable therewith having a particular disposition in relation to a focal point of the shock wave system for obtaining positional correlation with said first mentioned indexing means whereby each of the indexing means serves as a reference for the respective other one whereupon said focal point coincides with said particular geometric point in an imaging plane defined by the ultrasonic oscillator such that a concretion internal to the body may be imaged by the ultrasonic imaging device, and then comminuted by the shock wave system while the body remains fixedly positioned on the support means.

2. Apparatus as in claim 1, wherein said mounting means for the ultrasonic oscillator provides for movement of said oscillator on a surface of a sphere with additional adjustment in radial direction such that a principal axis of ultrasonic image production runs through the center of said sphere.

3. Apparatus as in claim 2, wherein said mounting means includes a first arc shaped rail to which is mounted pivotably, in cardanic fashion, a second arc shaped rail, the ultrasonic oscillator being mounted to the second arc shaped rail such that the first arc shaped rail is moveable over a first angular range, the second arc shaped rail is pivotable over a second angular range, vis-a-vis the first arc shaped rail, said means for mounting the first arc shaped rail being in addition pivotable about a vertical axis;

said mounting means being additionally translationally displaceable in three coordinate directions.

4. Apparatus as in claim 3 wherein the principal axis of the ultrasonic oscillator, the pivot axis for the inner rail and the turning axis for the guide means intersect in a common center of the two arcs.

5. Apparatus as in claim 1, said mounting means including means appearing within an ultrasonic imaging field of the ultrasonic oscillator to obtain an ascertainable, imaged marking vis-a-vis said center.

6. Apparatus as in claim 1, including a second ultrasonic imaging oscillator having a fixed relation to said shock wave focusing device so as to be oriented towards the focusing center thereof.

7. Apparatus in claim 1, said mounting means including first means for shifting a suspension point in all three dimensions; and second means suspended from the suspension point and provided for mounting said ultrasonic oscillator such that it is able to point towards said particular geometric point from any direction.

8. Apparatus as in claim 1, further comprising means for tracking the location of the geometric point as adjusted and for tracking any angular adjustment of the ultrasonic oscillator.

* * * * *